United States Patent
Thomson et al.

(10) Patent No.: US 10,878,312 B2
(45) Date of Patent: Dec. 29, 2020

(54) QUANTITATIVE ASSESSMENT OF BIOLOGICAL IMPACT BY SCORING DIRECTED TREE GRAPHS OF CAUSALLY INCONSISTENT BIOLOGICAL NETWORKS

(71) Applicants: Selventa, Inc., Cambridge, MA (US); Philip Morris Products, S.A., Neuchatel (CH)

(72) Inventors: Ty Matthew Thomson, Arlington, MA (US); Dmitry Vasilyev, Somerville, MA (US); Florian Martin, Peseux (CH)

(*) Notice: Subject to any disclaimer, the term of this patent is extended or adjusted under 35 U.S.C. 154(b) by 619 days.

(21) Appl. No.: 14/751,204

(22) Filed: Jun. 26, 2015

(65) Prior Publication Data
US 2015/0294218 A1 Oct. 15, 2015

Related U.S. Application Data

(63) Continuation of application No. PCT/US2013/077910, filed on Dec. 27, 2013.

(60) Provisional application No. 61/746,728, filed on Dec. 28, 2012.

(51) Int. Cl.
*G06N 3/06* (2006.01)
*G16B 5/00* (2019.01)

(52) U.S. Cl.
CPC .............. *G06N 3/061* (2013.01); *G16B 5/00* (2019.02)

(58) Field of Classification Search
None
See application file for complete search history.

(56) References Cited

U.S. PATENT DOCUMENTS

| | | |
|---|---|---|
| 2005/0038608 A1 | 2/2005 | Chandra et al. |
| 2005/0049987 A1 | 3/2005 | Meek et al. |
| 2005/0154535 A1 | 7/2005 | Sun et al. |
| 2005/0165594 A1 | 7/2005 | Chandra et al. |
| 2007/0225956 A1 | 9/2007 | Pratt et al. |
| 2009/0099784 A1* | 4/2009 | Ladd ................. G06F 19/12 702/19 |
| 2009/0307213 A1 | 12/2009 | Deng et al. |
| 2011/0307494 A1 | 12/2011 | Snow |

FOREIGN PATENT DOCUMENTS

| | | |
|---|---|---|
| EP | 0 984 366 A2 | 3/2000 |
| JP | 2005-243024 A | 9/2005 |
| JP | 2008-532460 A | 8/2008 |
| WO | WO-2011153200 A2 * | 12/2011 ............. G06F 19/12 |
| WO | WO 2012/168483 A1 | 12/2012 |

OTHER PUBLICATIONS

VanderWeele, Tyler J., and James M. Robins. "Signed directed acyclic graphs for causal inference." Journal of the Royal Statistical Society: Series B (Statistical Methodology) 72.1, 111-127 (Year: 2010).*
Klamt, Steffen, and Axel von Kamp. "Computing paths and cycles in biological interaction graphs." BMC bioinformatics 10.1, 181 (Year: 2009).*
Florian Martin et al., "Assessment of network perturbation amplitudes by applying high-throughput data to causal biological networks", BMC Systems Biology 2012, May 31, 2012, pp. 1-18.
David J. Aldous, "The Random Walk Construction of Uniform Spanning Trees and Uniform Labelled Trees", SIAM Journal on Discrete Mathematics, vol. 3, No. 4, Nov. 1, 1990, pp. 450-465.
Written Opinion of the International Searching Authority and International Search Report issued in International Application No. PCT/US2013/077910, dated Apr. 29, 2014, 9 pages.
Dmitry M. Vasilyev et al., "An algorithm for score aggregation over causal biological networks based on random walk sampling", BMC Research Notes, 2014, Aug. 11, 2014, pp. 1-10.
Extended European Search Report issued in European Patent Application No. 13868236.4, dated Aug. 16, 2019, 10 pages.
Japanese Notice of Reasons for Refusal issued in Japanese Patent Application No. 2015-550782, dated Oct. 24, 2017, 7 pages.
Canadian Office Action issued in Canadian Patent Application No. 2,896,732, dated Oct. 8, 2019, 5 pages.
European Communication pursuant to Article 94(3) issued in related European Patent Application No. 13868236.4, dated Feb. 7, 2020, 9 pages.

* cited by examiner

*Primary Examiner* — G Steven Vanni

(57) ABSTRACT

Disclosed herein are system, method, and computer program product embodiments for determining a score for a degree of activation of a biological network. An embodiment constructs a tree graph comprising a root node and a set of child nodes. The root node represents a biological network having a reference node and causal connections among a set of nodes that represent biological entities, biological processes, or other biological networks. Each child node represents a particular node in the biological network and is connected to the root node by a signed, directed edge pointing from the root node to that child node. Each child node also has an associated weight based on one or more paths connecting the child node to the reference node in the biological network. The embodiment further scores the tree graph based on scores assigned to the child nodes and the signs of the singed, directed edges.

20 Claims, 5 Drawing Sheets

G $t_1$ $t_2$ $t_3$

Spanning trees

QUANTITATIVE ASSESSMENT OF BIOLOGICAL IMPACT BY SCORING DIRECTED TREE GRAPHS OF CAUSALLY INCONSISTENT BIOLOGICAL NETWORKS

TECHNICAL FIELD

This disclosure relates generally to methods and techniques for characterizing the response of biological networks.

BACKGROUND OF THE RELATED ART

Networks provide a powerful framework for describing complex systems in many different areas, ranging from natural and social sciences to computer and electrical engineering. Their quantitative analysis is based on the concepts and properties studied in the mathematical field of graph theory. Leveraging this knowledge can help address challenging problems that arise in concrete situations.

Signed graphs are used in a variety of disciplines including systems biology, where a signed edge relating two nodes may represent the positive or negative regulatory relationship between two biological entities within a network. Recent advances in experimental and computational techniques have enabled systems-wide measurement of biological entities such as gene expressions or protein activities, and facilitated their integration into larger and larger networks. In this context, the derivation of systems-level properties integrating the levels of the individual biological entities with the corresponding graph structure has become of high interest, because it allows relating molecular mechanisms to overall system behavior.

The exposure of organisms to biologically active substances leads to complex responses, with the interplay between DNA, RNA, proteins, and other biological molecules coalescing to define the cellular phenotypes. Investigation of the resulting biological impact to yield coherent mechanistic insights requires methodologies that can leverage molecular profiling technologies that measure systems-wide changes in thousands of molecular species from a single experiment (e.g., transcriptomics, proteomics, or metabolomics).

A variety of approaches that partially address these investigational requirements have been developed. For example, to derive insight into individual mechanisms, transcriptomic data describing the differential gene expressions produced in response to an exposure can be interpreted in light of pre-defined sets of genes with similar functions or expression patterns (as defined by external databases, for example, MSigDB). Methods like Gene Set Enrichment Analysis (GSEA) or Reverse Causal Reasoning (RCR), which are based on the enrichment of these sets within the differentially expressed genes, enable qualitative investigation of experimental data in light of the statistical enrichment of mechanisms represented by each gene set, while other methods like Network Perturbation Amplitude (NPA) scoring provide quantitative assessment of the degree of perturbation of the mechanisms. It should be noted that the RCR and NPA approaches rely on gene sets that are causally downstream of each mechanism, and thus they allow identification (RCR) and quantitation (NPA) of mechanisms that are likely causes of the measured differential gene expression rather than their consequences (e.g., as assumed when activated pathways are identified based on the differential expressions of the transcripts corresponding to their constituting proteins). To gain systems-level mechanistic insights, findings for active molecular mechanisms can be linked to potential systems-level and phenotypic effects using biological networks comprised of relationships between molecules and processes. Such biological networks are available in variety of public and commercial databases (e.g. Kyoto Encyclopedia of Genes and Genomes (KEGG) Pathways). However, formal methods to integrate individual mechanistic findings and network-level relationships are required to assess the global biological impact of an active substance in a mechanistically coherent manner. They can be guided by the NPA approach that contains a first step in this direction, because it combines the individual mechanisms interconnected within a biological network into a single aggregated entity for which the degree of perturbation can be evaluated.

The ability to gain quantitative systems-level mechanistic insight into the effects of exposure to biologically active substances or other environmental insults (together referred to as "exposures") on biological networks using molecular profiling data has a variety of practical applications, from drug development to consumer safety. For example, candidate compounds can be screened for their ability to affect signaling in therapeutically-relevant pathways (e.g., inhibition of cell cycle), or the molecular mechanisms modulated by chemical exposure can be quantitatively evaluated for their possible association with health risk (e.g., induction of DNA damage). Both of these examples highlight the pressing need to assess the biological impact of exposure, whether the ultimate goal is therapeutic intervention or harm reduction. Recently, there has been an increased focus in systems toxicology on systems-oriented methodologies that emphasize understanding the biological impact of chemical exposures with increased mechanistic granularity. In particular, a recent report by the US National Research Council Committee on Toxicity Testing and Assessment of Environmental Agents advocates for a shift away from toxicological assessment at the level of apical endpoints and towards deriving systems-level understanding of the effects of an exposure on the affected toxicity pathways. In this context, approaches that can leverage network-level information together with quantitative assessments of mechanistic effects provide a powerful opportunity to offer true systems-level insights into the biological impact of an exposure.

Although the biological processes mentioned above are highly interconnected, the underlying biological mechanisms can be organized into distinct network models with defined boundaries in order to explicitly capture the cellular signaling pathways in each process. This segmentation enables the independent evaluation of each process that contributes to a distinct function within the cell. The signaling events within a network can be captured as causal relationships representing signed and directed cause-effect relationships (edges) between biological entities, processes, or even other networks (nodes). Because proteins and interactions are often involved in regulating multiple responses, nodes and edges can be shared among multiple networks, providing an explicit representation of the interactions between subnetworks.

Individual nodes within a network may represent entities or activities that can be experimentally measured, and together these measurements can provide insight into the overall function of the network. In addition to individually looking at measurements for individual nodes in the network, it can be advantageous to summarize these measurements into an overall "score" representing the net activation of the network. Furthermore, while it may not be possible to easily measure some of the nodes in a network, it may be possible to obtain a score for some of these nodes that have an associated signature of measurements. A score for one node can similarly combined with scores or measurements for other nodes in the network to provide an overall score for the activation of the network.

BRIEF SUMMARY

According to one aspect of this disclosure, a method of computing a score for a causally consistent network is provided by transforming the network into a HYP-like structure ("HYP" if the nodes have associated measurements, or "meta-HYP" if the nodes are themselves HYPs and have associated scores), and then applying known HYP scoring methods (e.g., Network Perturbation Amplitude (NPA), Geometric Perturbation Index (GPI), or the like) based on measurements or scores associated with nodes in the HYP/meta-HYP.

According to another aspect of this disclosure, a meta-HYP is created with weights associated with each downstream node to avoid overweighting measurements that contribute to scores for multiple HYPs in the network.

According to yet another aspect, a method is described for creating a HYP or meta-HYP with weights associated with each downstream node from a causally inconsistent network using one of the following techniques: sampling of spanning trees, maximal score spanning trees, or shortest path.

A further aspect of this disclosure is a method to transform a meta-HYP (with or without weights associated with each downstream node) into a HYP using the weights associated with each downstream gene (where the weights are based on the scoring algorithms intended at the meta-HYP and HYP levels). This approach applies if scoring methods at HYP and meta-HYP levels are linear functions.

A still further aspect of this disclosure is the application of the above-described framework and methods to construct and score meta-HYPs for "meta-networks," which are networks whose nodes that represent other networks.

The foregoing has outlined some of the more pertinent features of the subject matter of this disclosure. These features should be construed to be merely illustrative. Many other beneficial results can be attained by applying the disclosed invention in a different manner or by modifying the invention as will be described.

BRIEF DESCRIPTION OF THE DRAWINGS

For a more complete understanding of the disclosed subject matter and the advantages thereof, reference is now made to the following descriptions taken in conjunction with the accompanying drawings, in which.

DETAILED DESCRIPTION

Figure 1:
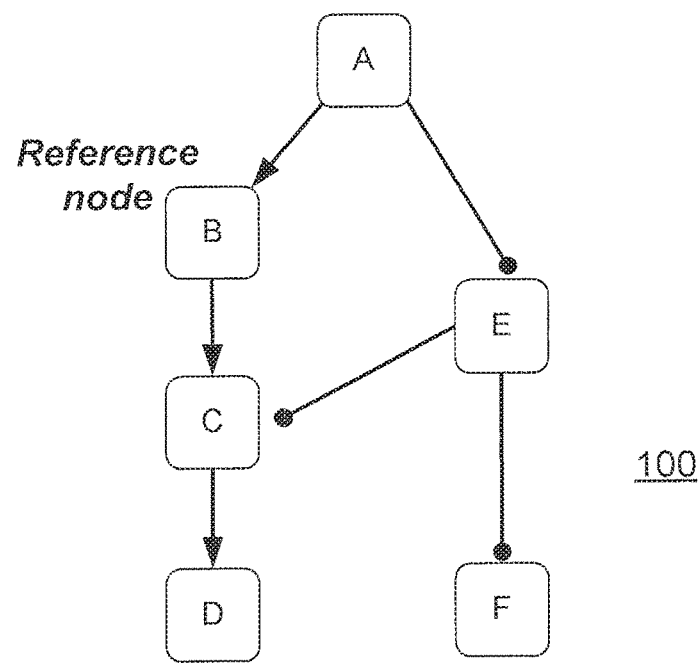
FIG. 1 illustrates a network composed of casual connections between nodes that represent biological entities, processes or other networks.

As used herein, the following terms have the following definitions:

A "knowledge base" is a directed network, preferably of experimentally-observed casual relationships among biological entities and processes;

A "node" is a measurable entity or process;

A "measurement node" is a measured entity or process;

A "reference node" represents a potential perturbation to a node;

A "signature" is a collection of measurable node entities and their expected directions of change with respect to a reference node;

A "differential data set" is a data set that has data associated with a first condition, and data associated with a second condition distinct from the first condition;

A "fold change" is a number describing how much a quantity changes going from an initial to a final value, and is specifically computed by dividing the final value by the initial value;

A "signed graph" (i.e., a graph with a signed edge) is a representational structure that, in the context of this disclosure, provides information concerning regulation and signaling in systems biology; in a signed graph, positive directed edges "→" capture activating relationships between two entities (e.g., protein activities), and negative directed edges "⊣" capture inhibitory relationships.

A "causally consistent network" is a balanced graph, and a "causally inconsistent network" is an unbalanced graph. As a functional definition, and for a causally consistent network, all paths between any given pair of nodes have the same net sign; for a causally inconsistent network, for any two nodes there exists at least one path with a positive net sign as well as at least one path with a negative net sign. The net sign is positive if there is an even number of "inhibits" or "decreases" edges along the path, and the net sign is negative if there are an odd number of "inhibits" or "decreases" edges along the path.

A "network model" is an interconnected hierarchy, with a top level network organized into one or more subnetworks, wherein signaling events within each subnetwork are captured as causal relationships representing signed and directed cause-effect relationships (edges) between biological entities (nodes) typically based on experimental evidence reported in primary literature. Because proteins and interactions are often involved in regulating multiple responses, many nodes and edges are shared among multiple subnetworks, thus providing an explicit representation of the interaction between subnetworks. At the base of the network model hierarchy are nodes that describe individual molecular mechanisms and that, within a given knowledgebase, may be causally upstream of gene sets representing increased or decreased gene expressions that have been observed upon direct experimental perturbation of the node. These nodes together with their downstream gene expression relationships are called HYPs.

A "HYP" is a particular type of network where one "source" node is connected to a set of measurable downstream nodes via causal edges. Typically, a HYP is a specific type of network model comprised of a set of causal relationships connecting a node representing a particular biological activity (e.g., the increase in abundance of activation of a particular kinase, or a more complex network model describing a growth factor signaling pathway) to measurable downstream entities (e.g., gene expression values) that it positively or negatively regulates. A HYP may also be considered a hypothesis subnetwork.

The networks, subnetworks and HYPs define a priori the range of biological responses that can be assessed within a given experiment.

Network Perturbation Amplitude (NPA) is a known method for assessing the degree of exposure-induced perturbations in biological entities from transcriptomic data. NPA scoring uses the relationships within a HYP to produce a score representing the change in abundance or activity of the corresponding individual or aggregated entity based on the magnitude and direction of changes of the downstream nodes in the HYP. The NPA method can be extended to produce scores for the changes in activity networks.

In particular, the methodology takes as inputs the differential measurements (for example, differential gene expression measurements) obtained for a set of contrasts (e.g., treated vs. control comparisons) to be evaluated and a network model that provides a coherent a priori description of a possible response captured in the experiment. The methodology then integrates the differential measurements with the network model to produce a score for each contrast.

Thus, NPA scoring typically consists in summing the contributions of each node of the network, adjusted by their relative signs with respect to the rest of the nodes in the network, as determined by the edges of the graph. Such an approach is used when the network is causally consistent (or "balanced" in the graph-theoretical language).

Another known technique for HYP scoring is GPI (Geometric Perturbation Index), which computes the mean treatment-induced differential expression of the genes included in the HYP. A formula for calculating GPI is described in PCT/EP/2012/061035.

FIG. 1 represents a network 100 that is composed of causal connections between nodes (A, B, C, D, E, and F) that represent biological entities, processes or other networks. In this network 100, the arrows represent causal increase relationships (e.g., node A increases node B, node B increases node C, and node C increases node D). The edges terminating in a circle represent causal decrease relationships (e.g., node A decreases node E, and node E decreases nodes C and F).

Figure 2:
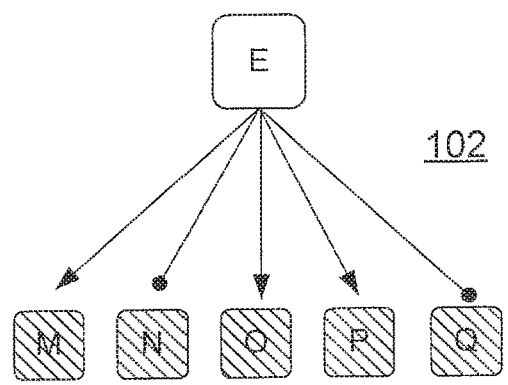
FIG. 2 illustrates a HYP, which is a particular type of network where one source node is connected to a set of measurable downstream nodes via causal edges.

FIG. 2 illustrates a HYP 102. As noted above, a HYP 102 is a particular type of network where one "source" node (here node E) is connected to a set of measurable downstream nodes (here nodes M, N O, P and Q) via causal edges. The measurable nodes are denoted by the diagonal hash indication.

Figure 3:
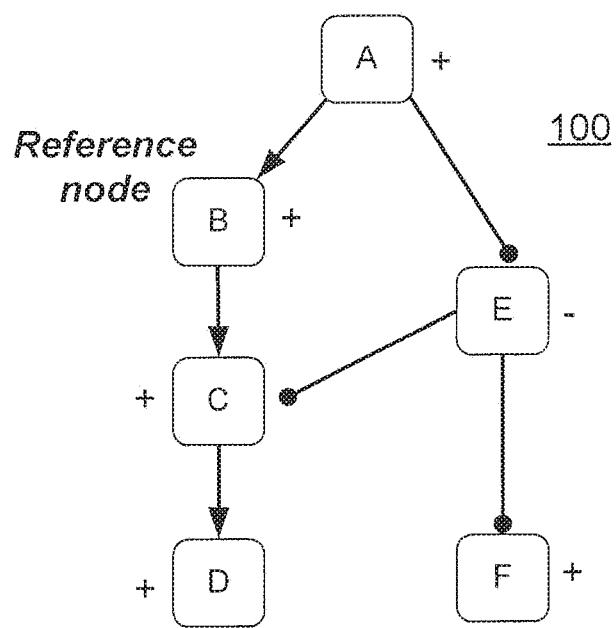
FIG. 3 illustrates the same network as shown in FIG. 1, with each individual node annotated with a sign indicating a net positive or negative causal relationship with a reference node in the network.

FIG. 3 illustrates the same network 100 depicted in FIG. 1, but each node is annotated with a "+" or "−" sign indicating a net positive or negative causal relationship with the reference node (here, node B) based whether that node is connected to the reference node via an even ("+") or odd ("−") number of causal connections via any path connecting those nodes.

Figure 4:
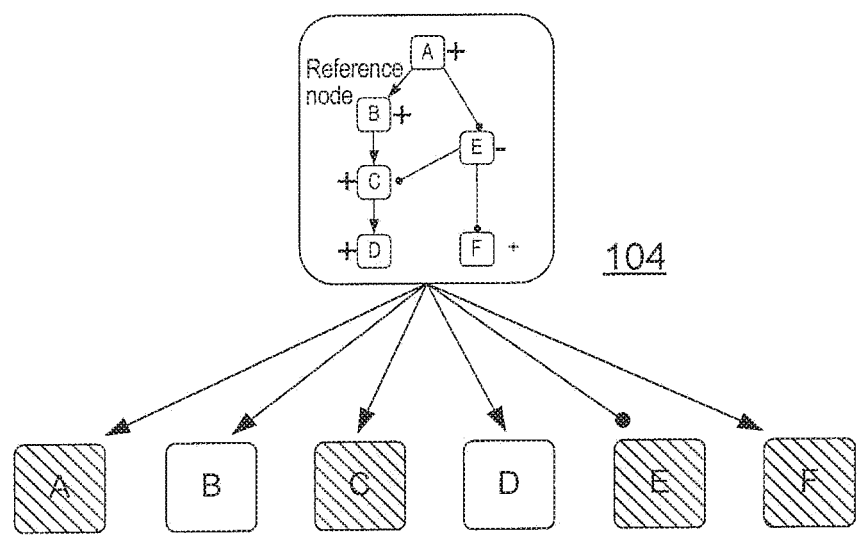
FIG. 4 illustrates the network in FIG. 3 converted into a HYP-like structure, referred to herein as a "meta-HYP"

FIG. 4 illustrates the network from FIG. 3 after it has been converted into a HYP-like structure, which is referred to herein as a "meta-HYP" 104. The meta-HYP is created by connecting a node representing the entire network to each node in the network with a causal increases or causal decreases depending on whether that node has a net positive or negative relationship (respectively) with the reference node. The measurable nodes in the meta-HYP are denoted by the diagonal hash indication.

Figure 5:
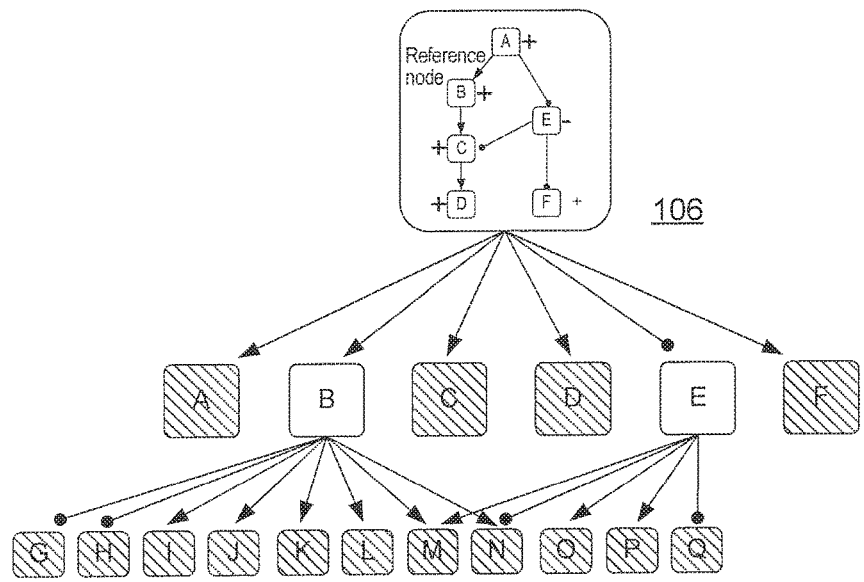
FIG. 5 illustrates a meta-HYP structure according to this disclosure.

FIG. 5 illustrates a meta-HYP 106 where some of the nodes are not measurable but are instead represented by HYPs (nodes B and E in this example) that, in turn, have measurable downstream nodes (e.g., nodes G through Q). The measurable nodes are denoted by the diagonal hash indication. Note that the HYP for node B and the HYP for node E both share the measurable downstream nodes M and N.

Figure 6:
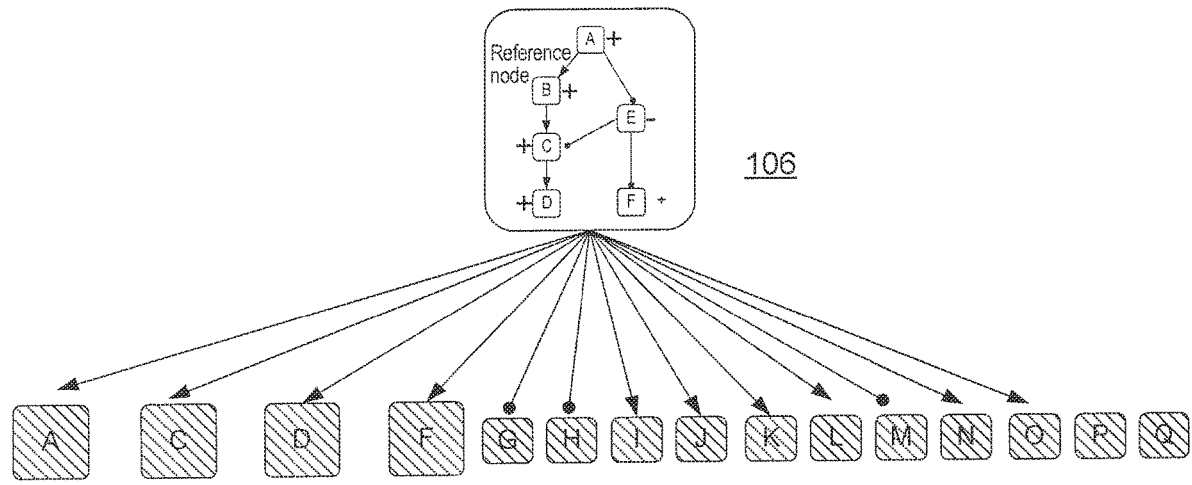
FIG. 6 illustrates the meta-HYP from FIG. 5 converted into a HYP structure according to this disclosure.

FIG. 6 illustrates the meta-HYP 106 from FIG. 5 after it has been converted into a HYP with all of the measurable entities from the meta-HYP and the downstream HYPs combined into a single set of HYP downstream measurable entities. Preferably, each measurable is assigned a weighting factor (not shown) during the HYP construction process.

Network Scoring for Causally Consistent Networks

The structure of the network guides aggregation of the node measurements and/or node HYP scores into a network score representing a change in the process described by the network. Specifically, and according to a first aspect of this disclosure, in certain embodiments the network is scored by first transforming the network into a HYP-like structure, and then applying HYP scoring methodology (as described previously, with some modifications as described below). The process of aggregating the nodes in a network into a single HYP-like structure requires that the network be causally consistent (called a "balanced graph" in graph theory), meaning that the net causal relationship between any two nodes in the network is independent of the path traversed between the nodes. According to this approach, a single node within the network is first selected as the "reference node," providing a reference point against which to evaluate the causal relationship of each other node in the network. For each node in the network, a path between that node and the reference node is first selected (any path between these two nodes will produce identical results for causally consistent networks). The path may be selected irrespective of the direction of the edges along that path (i.e., the path can traverse with ("downstream") or against ("upstream") the direction of the causal connections, or traverse any combination of upstream or downstream edges). The number of causal decrease edges along the path is counted, and if this is an odd number then the starting node has a net decrease relationship (i.e., net negative causal relationship) with the reference node, and if it is an even number then the starting node as a net increase relationship (i.e., net positive causal relationship) with the reference node. This process is illustrated in FIG. 3. A HYP-like structure is then constructed with a node representing the network serving as the upstream node ("source") for the HYP, and each node in the network downstream of this upstream node connected by a causal increase or decrease edge, depending on the net relationship with the reference node. This is illustrated in FIG. 4. The reference node is always connected to the source node via a causal increase edge.

By convention, if some of the nodes in the resulting HYP-like structure are not measured directly but are instead HYPs that can be scored via any HYP scoring method (e.g., the NPA or GPI algorithm), this HYP-like structure is called a meta-HYP (because it is a HYP of HYPs). This concept is illustrated in FIG. 5. If, however, only measurements for nodes in the network are considered (and not any HYP scores), then this HYP-like structure is just called a HYP. Functionally, there is no difference between a meta-HYP and a HYP, but by convention the meta-HYP is named distinctly to make it explicit that its score is derived from the scores of other HYPs. Here, and for simplicity, the meta-HYPs do not contain any measurable nodes, but meta-HYPs composed of both scored and measured nodes can also similarly be considered within the framework described herein.

In certain embodiments, HYP scoring algorithms can be employed directly to score HYPs that result from network aggregation. HYP scoring algorithms can also be employed for scoring meta-HYPs by substitution of scores in place of differential measurements for the downstream nodes that are themselves HYPs. For example, when the Strength formula is applied to score a meta-HYP, the formula becomes:

$$\text{Strength} = \sum_i W_i d_i \beta_i, \quad W_i = \frac{1}{N}$$

where $\beta_i$ is the score for downstream HYP i or the log-fold-change of the measurement for node i, $d_i \in \{-1,+1\}$ is a direction associated with the predicted regulation (increase or decrease) of node i in the meta-HYP, and N is the number of downstream nodes in the meta-HYP with associated scores or measurements.

Network Scoring for Causally Inconsistent Networks

For causally inconsistent models, the net causal relationship between any two nodes depends on which path is selected (i.e., some paths will have an odd number of causal decrease edges, while other paths between the same two nodes will have an even number of causal decrease edges). Thus, the straightforward meta-HYP construction process outlined above is not possible.

Shortest Path

According to another embodiment, one method for constructing a meta-HYP from a causally-inconsistent network is to identify the shortest path with a net positive causal relationship between each node and the reference node, and the shortest path with a net negative causal relationship between each node and the reference node. For each node, if the shortest positive path is shorter than the shortest negative path, then that node is assigned a causal increase in the meta-HYP, and if the shortest positive path is longer than the shortest negative path, then that node is assigned a causal decrease in the meta-HYP. Nodes whose shortest positive and negative paths are the same length are omitted from the meta-HYP. When computing the length of paths between two nodes, each edge may have the same "length" resulting in the lengths representing the number of edges in the path. Alternatively, if there are multiple types of increase and decreases edges in the network, different types of edges may have different "length" contributions to the overall path length. For example, direct causal increase or decrease edges may have a shorter length than causal increase or decrease edges that are not explicitly denoted as direct relationships. This method is called the "Shortest Path" method for resolving causally inconsistent networks and producing meta-HYPs.

Another embodiment for constructing a meta-HYP from a causally inconsistent network involves estimating a relative degree of increase or decrease that each node has with respect to the reference node, rather than an absolute determination of increase or decrease. Such methods will produce a meta-HYP where each causal edge connecting to a downstream node is additionally associated with a weighting factor $s_i$ between 0 and 1 that describes the degree of increase of decrease of that edge. Because these weighting factors pertain to the sign (increase or decrease) associated with each edge in the meta-HYP, they are referred to as sign weights.

Random Walk

According to an embodiment, one method for computing sign weights involves performing repeated random walks over the network, where each random walker has an internal state of "+" or "−", and further assigns its current state to each node the first time it visits that node. Note that during its traversal of the network, each walker in the algorithm can also produce a valid spanning tree, and the set of spanning trees from all walkers is known to produce a representative sample among all spanning trees of the signed graph. In this embodiment, the method combines the spanning trees to produce a single meta-HYP for the network, and thus this method is called the Sampled Spanning Tree (SST) method. The following section provides additional details regarding this approach.

The SST Method

Given a balanced signed graph G=(Nodes,Edges) and a quantity $X_n$ defined on all its nodes (e.g., gene differential expression, or inferred perturbation amplitude[3], etc.), the aggregation of $X_n$ over G is defined as $$X_G = \sum_{n \in Nodes} s_{n \to REF}(G) \cdot X_n \quad (1)$$

where $S_{n \to REF}(G) \in \{-1,1\}$ is the nodal sign given by the product of the edge signs over any path in G relating n and one reference node REF. Because G is a balanced graph, $S_{n \to REF}(G)$ is independent of the chosen path and is therefore defined unambiguously for all nodes n ($S_{n \to REF}(G)$ is the "relative sign with respect to the rest of the nodes in the network"). Note that the edge directions in a directed signed graph are not relevant in the present context.

The SST method is based on the concept of spanning tree: t is a spanning tree of G if t is a subgraph of G that is a tree and that connects all nodes of G. One useful property of spanning trees comes from the fact that the aggregated quantity $X_G$ defined in Eq. (1) can be equally rewritten in term of any t as:

$$X_G = X(t) = \sum_{n \in Nodes} s_{n \to REF}(t) \cdot X_n \quad (2)$$

where $S_{n \to REF}(t) \in \{-1,1\}$ is now calculated over one single path in $t \subset G$ between node n and the reference node REF. Suppose all spanning trees $t_1 \ldots t_{N(G)}$ of G can be enumerated, then $X_G$ can be equivalently rewritten as.

$$X_G = \frac{1}{N(G)} \sum_{t=t_1 \ldots t_{N(G)}} \quad (3)$$

$$X(t) = \frac{1}{N(G)} \sum_{t=t_1 \ldots t_{N(G)}} \sum_{n \in Nodes} s_{n \to REF}(t) \cdot X_n$$

An important benefit about the SST method is that Eq. (3) is well-defined, even if G is an unbalanced graph. This property results from the fact that the enumeration of the spanning trees is independent of the edge signs (i.e. "→" or "⊣") and from the fact that $S_{n \to REF}(t)$ is unambiguously defined for a given spanning tree t. Swapping the summations over spanning trees t and nodes n in Eq. (3) yields the final expression:

$$X_G = \sum_{n \in Nodes} s_{n \to REF}(G) \cdot X_n \quad (4)$$

where $$S_{n \to REF}(G) = \frac{1}{N(G)} \sum_{t=t_1 \ldots t_{N(G)}} s_{n \to REF}(t) \quad (5)$$

Eq. (4) extends the initial definition of $X_G$, which is valid for balanced graphs only. It replaces the discrete nodal sign $S_{n \to REF}(G) \in \{-1, +1\}$ by the continuous nodal effective weights $S_{n \to REF}(G) \in [-1, +1]$ in the case of unbalanced graphs. They represent a "topological average" over all possible spanning trees for which a well-defined aggregation of $X_n$ over G can be calculated. The nodal effective weights $S_{n \to REF}(G)$ also generalize beyond the specific aggregation method here (Eq. (1)), and represent a generally applicable "topologically averaged" signed relationship between two nodes (n and REF) in an unbalanced graph.

In practice, the explicit enumeration of all the spanning trees becomes unrealistic for large unbalanced graphs. Thus, preferably another aspect of the SST method involves replacing the exhaustive sum over all spanning trees $t_1 \ldots t_{N(G)}$ in Eq. (5) by an approximation involving a computable representative subset of spanning trees T(G). One computational approach to this is to apply the Aldous method, which generates a suitable uniform sample of spanning trees using random walks over the graph. In particular, this computational method comprises moving "signed" walkers along the graph, whose trajectory and sign $\in \{-1, +1\}$ are determined by the following set of local rules (assuming that G is connected):

1. Each walker starts at the reference node REF, with positive sign "+1".
2. The walker randomly chooses an edge connected to the current node to traverse. The edge choice is irrespective of the sign or direction of the edge.
3. The walker's sign is preserved if it traverses an "increases" edge ("→") and is flipped if it traverses a "decreases" edge ("⊣").
4. If the next node has not already been visited by that walker, the walker marks the next node as visited and assigns its sign to that node.
5. If the next node has already been visited by that walker, then the walker adopts the sign from the node.
6. Continue until all nodes of the graph are visited.

In the framework of Aldous' method explained above, Eq. (5) can be replaced by $$S_{n \to REF}(G) \approx \frac{N_+(n, G) - N_-(n, G)}{N_+(n, G) + N_-(n, G)} \quad (6)$$

where $N_\pm(n,G)$ records the number of random walker visiting node n with positive/negative sign. $N_+(n,G)+N_-(n,G)$ is the total number of sampled spanning trees in T(G), which is chosen to ensure convergence of the $S_{n \to REF}(G)$ approximations. Note that the sampled spanning trees $t \in T(G)$ are not needed explicitly for computing $S_{n \to REF}(G)$ in Eq. (6). They can be however reconstructed for a given walker by collecting all the edges traversed during Step 4.

Validation of the SST Method

Figure 7:
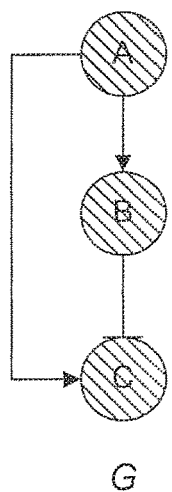
FIG. 7 illustrates a causally inconsistent network.
Figure 8:
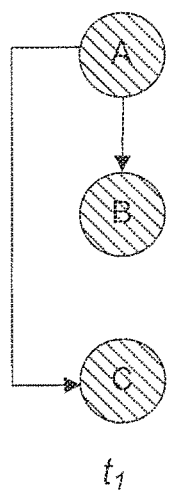
FIG. 8 illustrates the spanning trees corresponding to the causally inconsistent network in FIG. 7.
Figure 8:
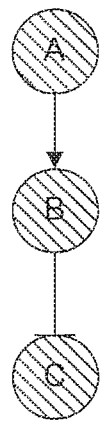
Figure 8:
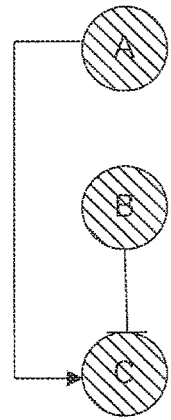

For illustration purposes, the SST method is first applied to the incoherent feed-forward loop (IFFL) case shown in FIG. 7. In this example network, the two paths "A→B" and "A→C⊣B" relating nodes A and B do not have the same sign, as defined by the product of the signs of their concatenated edges. The same holds for the node pair (A,C) and indicates that the relative sign of node A with respect to the remaining network nodes B and C is ambiguous. These observations correspond to the case of causally inconsistent networks or "unbalanced" graphs, for which an aggregation procedure cannot be performed unambiguously. FIG. 8 illustrates the spanning trees for the network in FIG. 7. Because the three spanning trees $\{t_1, t_2, t_3\}$ compatible with the corresponding graph are easily constructed, the sampling part of the SST method is not required (in this example). Then, Eq. (5) yields directly the following aggregation weights: $(S_{A=REF}, S_{B \to A}, S_{C \to A}) = (1, 0.333, 0.333)$. Now, assuming the following node values $X_A = X_B = X_C = 1$, which can typically correspond to gene differential expressions, then Eq. (4) gives an aggregated value $X_{IFFL} = 1.667$. This result is smaller than the sum of the individual values, reflecting the fact that these node values $X_n$ are not concordant with the edge B⊣C of the graph. In terms of spanning trees, Eq. (3) yields $(X(t_1), X(t_2), X(t_3)) = (3,1,1)$. This result shows that the spanning tree $t_1$ provides the highest contribution to $X_{IFFL}$, which is due to the fact that it does not contain the discordant edge B⊣C. Using other node values $X_n$ enables similar considerations to be made. From this simple example, it can be concluded that the aggregation based on spanning tree gives quantitatively consistent results and that both the node-based and the spanning tree-based representations can be meaningfully used to interpret its results.

To further validate the approach, the SST method was applied to complex causally inconsistent networks that have been constructed to faithfully describe real biological processes in the lung, and therefore include negative feedback and contradictory regulatory relationships. For many of these networks, a small number of edges were removed to reduce the causally inconsistent networks into causally consistent networks that are biologically closest to the desired causally inconsistent networks. The decision to remove an edge was made based on the expected/desired causal relationships between each node and the reference node. For example, feedback loops were edited such that the negative regulators were negatively related to the network through their inhibitor activity, instead of positively related to the network through their transcriptional regulation. In doing so, it was then possible to compare the SST results calculated on the causally inconsistent networks with the aggregation results obtained on the corresponding pruned causally consistent network versions. This provides an opportunity for testing the SST algorithm from both computational and biological points of view.

Because of the particular semantics of the language used to encode these network models, Step 2 of the random walk rules described above was modified to account for extra granularity in the networks. Intramolecular edges relating a protein and its activity carry a higher relevance, and thus a higher likelihood of being retained in the spanning tree than direct intermolecular edges relating the activities of two causally-linked but different proteins that are known to directly interact. Indirect intermolecular edges relating the activities of two causally linked proteins that are not known to interact directly carry the lowest weight. This resulted in the following slightly adapted rule for Step 2:

2. For each node, a walker randomly chooses an edge to traverse, according to probabilities of each edge. The relative probabilities are:
   a. Intramolecular edges (relationships between molecules and their activities): 1
   b. Direct intermolecular edges (directly binds and increases/decreases): ½
   c. Indirect intermolecular edges (increases/decreases): ⅓
   d. Expression edges (relationships leading to changes in RNA abundance): ¼

Figure 9:
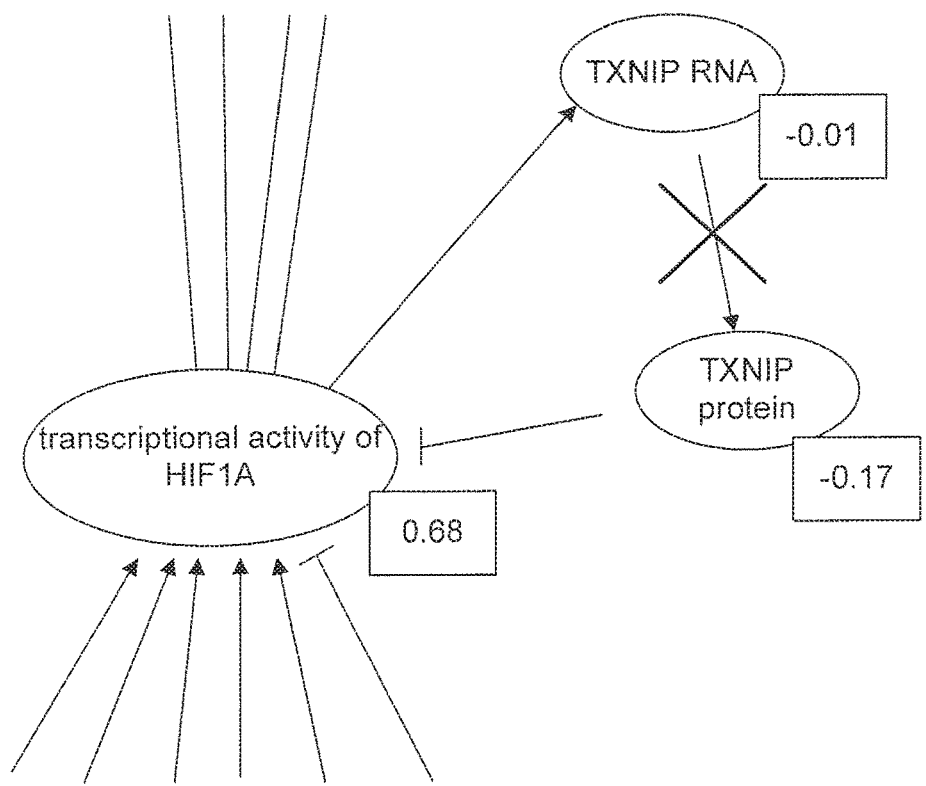
FIG. 9 illustrates a portion of a representative network against which the SST method was tested.

The SST method adapted in this manner was then run on the "Hypoxic Stress" network containing 144 nodes and 241 edges. Using 1,000 spanning trees was sufficient to produce nodal weights $S_{n \to REF}(G_{HS})$ (as given by Eq. (6)) with a median difference of less than 0.01 from the nodal weights using 20,000 spanning trees (maximum difference less than 0.05). In parallel, a manual biological investigation was performed to produce a pruned causally consistent version of the network that preserves its biological integrity by removing 4 edges. The comparison between the SST effective nodal weights $S_{n \to REF}(G_{HS})$ and the unambiguous nodal signs $s_{n \to REF}(G_{HS,PRUNED})$ identified only a single node that differed at the sign level. A closer examination of the SST results revealed an interesting configuration in the region of the network magnified on FIG. 9, namely, a causal inconsistency is present between the transcriptional activity of HIF1A (Hypoxia-inducible factor 1-alpha), the abundance of TXNIP (Thioredoxin-interacting protein) RNA, and the abundance of TXNIP protein. This causal inconsistency is indicated by the two paths TXNIP protein −|HIF1A transcriptional activity, and TXNIP protein←TXNIP protein←HIF1A transcriptional activity with opposite signs. The SST results indicate that the first path is preferred: TXNIP protein has a negative sign and HIF1A has a positive sign, in agreement with their connecting "decrease" edge ("−|"). Furthermore, the SST effective weights for the RNA abundance of TXNIP is very close to zero, meaning that the sign of this node is largely ambiguous and thus this node has little contribution to the aggregation. From the biological point of view, the edge connecting the TXNIP RNA node to the protein node was chosen to be removed, because the protein abundance and activity of TXNIP are negative regulators of the pathway, and thus should have a negative contribution to the aggregated network score. These considerations are compatible with the SST results. This particular case illustrates that the SST method is scalable to more complex networks and that its results are reflecting the biological content of the network.

Figure 10:
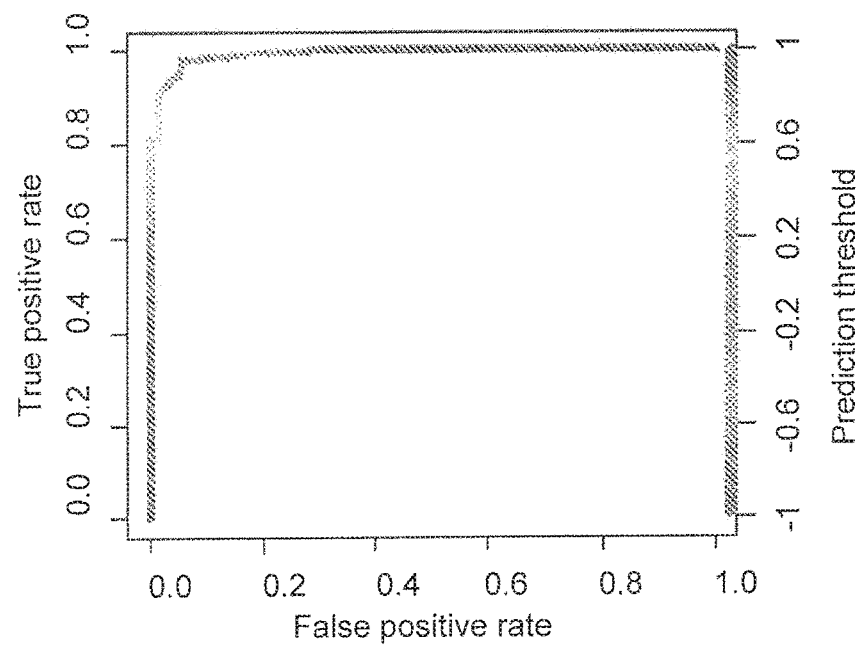
FIG. 10 illustrates the receiver operating characteristic (ROC) curve (true positive rate vs. false positive rate) for comparisons between the SST effective node weights $S_{n \rightarrow REF}$ and the corresponding nodal signs $s_{n \rightarrow REF}$ for a number of sample networks.

The SST method was further validated by benchmarking its performance against a set of graphs that were manually pruned to become causally consistent, similarly to the Hypoxic Stress network discussed above. Over a set of 81 (=15+7+32+23) networks contained in various cell proliferation, cellular stress, DACS, and pulmonary inflammation publications, 26 (=7+5+2+12) were causally inconsistent and 19 (=4+2+2+11) could be manually transformed into causally consistent networks using the same requirement as described above. The SST method was used to compute the effective nodal weights $S_{n \to REF} \in [-1, +1]$, which were then compared with the nodal signs $s_{n \to REF} \in \{-1, +1\}$ defined on the corresponding manually resolved networks. From the perspective of a classification problem where $S_{n \to REF}$ give the predictions and $s_{n \to REF}$ the actual values, the SST method was found to exhibit high accuracy, with a 4.4% rate of mislabeling directions (using zero threshold for the $S_{n \to REF}$ values, and averaging across all networks; mislabeling rate ranged from 0% to 19% for individual networks). The overall AUROC (area under the ROC curve) measured for the SST method was 0.992 (ranging from 0.90 to 1.0 for individual networks), and the majority of mislabeling events occurred with effective nodal weights near zero, as indicated in FIG. 10. These results show that the conclusions drawn for the SST method in the case of the Hypoxic Stress network could be extended to other networks, which definitely supports the reliability of the approach.

Finally, the SST method was also used for nodal value aggregation, specifically applying Network Perturbation Amplitude (NPA) and Biological Impact Factor (BIF) scoring calculations involving gene expression data. Note that because the SST method is not data-driven, gene expression data do not change the content of its results, rather they offer a different perspective on the comparison between $S_{n \to REF}$ and $s_{n \to REF}$ presented above. For this purpose, a public data set was used; this data set describes the effect of TNF treatment of normal human bronchial epithelial (NHBE) cells (ArrayExpress identifier E-MTAB-1027). Of the 19 biological networks (Hedgehog, Notch, Nuclear Receptors, PGE2, Hypoxic Stress, Osmotic Stress, DNA Damage-Components affecting TP63 Activity, Replicative Senescence, Dendritic Cell Activation, Macrophage Activation, Macrophage Differentiation, Mast Cell Activation, Megakaryocte Differentiation, NK Cell Activation, Neutrophil Chemotaxis, Neutrophil Response, Tc Response, Th1 Differentiation, and Th17 Differentiation), the tissue contexts of eight networks were consistent with NHBE cells. The NPA GPI scores of these eight networks were computed using the SST effective nodal weights $S_{n \to REF}$ for their causally inconsistent version and the nodal signs $s_{n \to REF}$ for their pruned causally consistent version. For each network, the paired values were compared across the 16 possible contrasts (four treatment doses and four time points). Six of the eight networks displayed correlations about 0.9. Notch exhibited poor correlation (0.540), as did Replicative Senescence (−0.081), the latter which results from the fact that all of the nodes with different signs for $S_{n \to REF}$ and $s_{n \to REF}$ lie in a single causally inconsistent region of the network that relates the impact of replicative senescence on MAPK signaling. The latter example points out that, although the SST method is able to produce nodal directions that are generally consistent with expectations, it may also be desirable to investigate resulting findings in light of the specific biology induced in an experiment and described by the networks. In the above example, TNF-mediated activation of MAPKs led to a large impact on the Replicative Senescence network through a minority of network nodes in a single region of the network. Given the fact that this region contained a causal inconsistency that was resolved by the SST method, additional focus can then be given to investigate the findings to ensure they are biologically relevant.

The following provides a generalization of the above-described SST technique. To that end, and without intending to be limiting, the walker's traversal rules are described below:

1. Each walker starts at the reference node, with the initial internal state of "+";
2. At each iteration, the random walker randomly chooses a causal edge connected to its current node to traverse; Different types of edges may have different relative probabilities to bias the random walk. For example, one may choose to bias the random walker to be twice as likely to traverse a direct causal increase or decrease edge compared to a causal increase or decrease edge that is not explicitly denoted as direct relationships.
3. The walker's internal state is preserved if it traverses an "increases" edge, and is flipped if it traverses a "decreases" edge;
4. If the next node has not already been visited by that walker, the walker marks the node with its current internal state;
5. If the next node has already been visited by that walker, then the walker adopts the sign from the node;
6. Repeat steps 2-5 until all causally connected nodes of the subnetworks are visited by that walker; and
7. Repeat this procedure for a large number of walkers (e.g., 1000).

When all walkers have finished traversing the network, according to one embodiment a sign weight $s_i$ for each node i is computed using the following formula:

$$s_i = \left| \frac{N_i^{up} - N_i^{down}}{N_i^{up} + N_i^{down}} \right|$$

where $N_i^{up}$ and $N_i^{down}$ denote the number of walkers that marked the node i with "+" and "−" signs, respectively. If $N_i^{up}$ is greater than $N_i^{down}$, then more random walkers reached node i from the reference node with a positive sign than with a negative sign, and node i is thus connected to the source node of the meta-HYP with a causal increase edge. If $N_i^{up}$ is less than $N_i^{down}$, then more random walkers reached node i from the reference node with a negative sign than with a positive sign, and node i is thus connected to the source node of the meta-HYP with a causal decrease edge. Each edge is additionally annotated with the sign weight $s_i$ indicating the degree to which that node is positively or negatively related to the source node. If $N_i^{up}$ equals $N_i^{down}$, then the same number of random walkers reached node i with a positive and negative sign. In this scenario, the node can be dropped from the meta-HYP (or alternatively assigned an increases relationship with a sign weight $s_i$=0.)

Given the sign weights determined by the SST method, meta-HYP scores can be computed using HYP scoring algorithms with some minor modification to incorporate weights associated with each node. For example, when the Strength formula is applied to score a meta-HYP with sign weights, the Strength formula becomes:

$$\text{Strength} = \sum_i W_i d_i \beta_i,$$

$$W_i = \frac{s_i}{\sum_j s_j}$$

where $\beta_i$ is the score for downstream HYP i or the log-fold-change of the measurement for node i, $d_i \in \{-1, +1\}$ is a direction associated with the predicted regulation (increase or decrease) of node i in the meta-HYP, $s_i$ is the sign weight, and $W_i$ is the net weight associated with each node. Here, the net weight is only dependent on the sign weight, but this formulation with a net weight become important when considering additional methods for modifying meta-HYPs in a manner that introduces additional weights to each node (see Accounting for HYP Overlaps below).

An alternative method for producing a meta-HYP for causally inconsistent networks also leverages the results of the same random walk procedure used in the SST method. Rather than combine the results from each walker into a single sign weight associated with each node in the network, this method uses the set of signs assigned to each node from each individual random walker to produce a different meta-HYP for each random walker. A score for each meta-HYP is computed for each contrast in the data set, and the meta-HYP with the largest absolute score for each contrast is identified and selected for that contrast. The meta-HYP with the highest magnitude score is the one that is most consistent with the underlying scores and/or differential measurements. Alternatively, the method may select the meta-HYP that has the highest absolute average score across all contrasts. In this view, the method is identifying the meta-HYP and associated spanning-tree with the highest magnitude score, and thus the method is called the Maximal Score Spanning Tree (MSST).

Summarizing, the above section describes a solution for defining signed relationships between nodes in an unbalanced graph the SST method. As has been described, this method uses the concept of a spanning tree as the minimal structure to enable a well-defined relationship between pairs of nodes. A continuous measure of the relationship between two nodes is then defined by averaging over a representative sample of spanning trees constructed using random walks over the signed graph. From that perspective, an unbalanced graph can be viewed as an "excessively rich" signed graph for which pairwise nodal relationships, and thus an original aggregation procedure, cannot be unambiguously defined. By summing over a representative sample of spanning trees compatible with the graph, no information is discarded during the extended aggregation procedure, so that the biological content of the network is preserved.

The SST method uses random walks to aggregate nodal values over arbitrary signed graphs, including large "causally inconsistent" networks. This approach provides for a representative sampling among all spanning trees of the graph and an approximation of the nodal effective weights as an average over all the sampled spanning trees. The SST method is applicable in a variety of situations requiring the aggregation of nodal values (e.g. gene differential expression, nodal NPA scores, etc.) over a signed graph and is scalable to arbitrary graph size.

Accounting for HYP Overlaps

Many HYPs may be supported by overlapping sets of measurements (see, FIG. 5), leading to interdependences between their scores, a decreased ability of these scores to capture the biology specifically perturbed in these HYPs, and ultimately interfering with our ability to derive specific mechanistic insights. To reduce the effects of such overlaps, the meta-HYP scoring process is modified to adjust the contribution $w_i$ of each HYP i to the meta-HYP score based on how much that HYP overlaps with other HYPs in the meta-HYP. This process provided the highest weight to unique subnetworks, and lower weights to subnetworks that were similar to other subnetworks.

To quantify how much overlap exists between downstream HYPs in a meta-HYP, the expected correlation between HYP scores may be calculated as follows. Consider two HYPs (two constant vectors) $e_1$ and $e_2$ with N downstream measurements (values are 0 for genes not in the HYP, −1 for genes connected by a causal decrease relationship, and +1 for genes connected by a causal increase relationship), and a differential measurement vector X for the measurements in the HYPs (a random vector with N independent components, not necessarily Gaussians, having the same standard deviation a). The cosine between the vectors $e_1$ and $e_2$ provides a measure of the similarity of the measurements supporting these HYPs. Furthermore, for the Strength scoring method, it is straightforward to show that the cosine between $e_1$ and $e_2$ is the expected correlation between the scores for these two HYPs for any set of measurements:

$$S_1 = e_1^T X,$$
$$S_2 = e_2^T X$$
$$\mathrm{corr}(S_1, S_2) = \frac{e_1^T e_2}{\|e_1\|\|e_2\|} = \cos(e_1, e_2).$$

In one embodiment, the overlap weights $w_i$ are then calculated using expected correlation matrix, using an inverse absolute row-sums of the corresponding rows. In general, the larger the absolute row-sum, the more corresponding subnetwork is correlated with the others. Specifically, the overlap weights may be computed as:

$$w_i = \frac{1 / \sum_j |\cos(e_i, e_j)|}{\sum_i \left(1 / \sum_j |\cos(e_i, e_j)|\right)}$$

When the Strength formula is applied to score a meta-HYP with such weighting factors, the formula becomes:

$$\mathrm{Strength} = \sum_i W_i d_i \beta_i,$$
$$W_i = \frac{w_i}{\sum_j w_j}$$

where $\beta_i$ is the score for downstream HYP i or the log-fold-change of the measurement for node i, $d_i \in \{-1 + 1\}$ is a direction associated with the predicted regulation (increase or decrease) of node i in the meta-HYP, and $w_i$ is the overlap weight of node i as defined above.

In general, multiple weights associated with a downstream node in a HYP can be combined into a single weight $W_i$ by multiplying the weights together and normalizing by the sum across all nodes of the product the weights for each node. For example, to combine the overlap weights and the sign weights into a single weight for each node in a meta-HYP:

$$W_i = \frac{s_i w_i}{\sum_j s_j w_j}$$

Converting Meta-HYPs into HYPs

When scoring meta-HYPs using NPA methods that compute a score as a linear combination of the underlying scores or differential measurements, it is possible to reformulate the meta-HYP as a direct function of the differential data underlying the downstream HYPs. The following describes this approach. This transformation is useful in that it enable HYPs constructed directly and HYPs constructed from networks to be treated equivalently.

To construct a HYP from a meta-HYP, according to one embodiment, first formulate the score for the meta-HYP as a function of the underlying HYP scores (for example, using the Strength formula). Next, substitute the formula for each HYP score into the meta-HYP score equation. As long as the meta-HYP and HYP scoring functions are linear combinations of the underlying components (HYP score for meta-HYPs, measurables for HYPs), this formula represents a linear combination of measurements underling the HYPs in the meta-HYP. The contributions of measurables downstream of multiple HYPs can be assembled into a single term per measurable by summing the contributions from each HYP. A HYP for the meta-HYP is then constructed based on the analytic formula for the meta-HYP score (which is expressed as an analytic function of the measurable in each downstream HYP). In particular, each measurable appears as a downstream in the HYP, and the sign of the edge relating the network source node to each measurable is based on the sign of the contribution of that node to the score. Measurables with positive contributions are connected via a causal increase relationship, and measurables with negative contributions are connected via a causal decrease relationship. Furthermore, a weighting factor equal to the absolute value of the contribution (the coefficient in front of the measurable in the meta-HYP formula) is assigned to each downstream measurable. The meta-HYP thus is represented by a HYP with weighted contributions from each downstream measurable. Note that when a HYP is constructed in this manner from a meta-HYP there is no requirement that the weighting factors sum to 1.

Consider the following strength formula for a meta-HYP:

$$\mathrm{Strength} = \sum_i W_i d_i \beta_i$$

Here $\beta_i$ represents the score for downstream HYP i or the log-fold-change of the measurement for node i. Considering these two cases separately, where A is the set of nodes in the meta-HYP that are represented by HYP scores, and B is the set of nodes in the meta-HYP that are represented by measurements.

$$\mathrm{Strength} = \sum_{j \in B} W_j d_j \beta'_j + \sum_{k \in A} W_k d_k \beta''_k$$

where $\beta'_j$ represents the log-fold-change of the measurement for node $j \in B$, and $\beta''_k$ represents the score for downstream HYP $k \in A$. If the HYP score for each k is computed by a linear HYP scoring method, then we can generically represent the formula for each $\beta''_k$ as:

$$\beta''_k = GPI_k = \sum_{l \in A_k} \alpha_l \beta'_l$$

where $\beta'_l$ represents the log-fold-change of the measurement for node l in the set $A_k$ of downstream nodes in HYP k, and where the term $\alpha_l$ includes any weighting factor (e.g., $W_k$), scaling factor (e.g., 1–$\mathrm{pval}_l$ for the GPI HYP scoring method), and direction $d_j$. Given such a score representation for each HYP k in the meta-HYP, we can formulate the meta-HYP score as:

$$\text{Strength} = \sum_{j \in B} W_j d_j \beta'_j + \sum_{k \in A} W_k d_k \sum_{l \in A_k} \alpha_l \beta'_l = \sum_{j \in B} W_j d_j \beta'_j + \sum_{k \in A} \sum_{l \in A_k} W_k d_k \alpha_l \beta'_l$$

As this formula is merely a weighted sum of the log-fold-changes of measurements, weights for each measurement that occur in multiple terms (i.e., appear as downstream measurements in multiple HYPs in the meta-HYP) can be summed together. The meta-HYP strength can thus be represented as:

$$\text{Strength} = \sum_m \alpha_m \beta'_m$$

where $\beta_m'$ represents the log-fold-change of the measurement for node m that appears as a downstream in any HYP in the meta-HYP, and where the term $\alpha_m$ is the net weighting factor associated with measured node m. In this form, the score for the meta-HYP has been cast into a direct function of log-fold-changes of measurements. The meta-HYP can thus be replaced with a HYP, where the sign of the edges connecting the source node (representing the network) to the downstream nodes m is given by the sign($\alpha_m$) (negative being causal decrease edge, positive being causal increase edge), and the weighting factor associated with each node m is given by $|\alpha_m|$. Given the ability to convert a meta-HYP into a HYP, this framework can additional be extended to any HYP-like structure where downstream nodes are represented by other meta-HYPs or HYPs.

Enabling Technologies

The techniques described herein are implemented using computer-implemented enabling technologies such as described in commonly-owned, co-pending applications U.S. Publication No. 2005/00038608, No. 2005/0165594, No. 2005/0154535, and No. 2007/0225956. These patent applications, the disclosures of which are incorporated herein by reference, describe a casual-based systems biology modeling tool and methodology. In general, this approach provides a software-implemented method for hypothesizing a biological relationship in a biological system that uses a database comprising a multiplicity of nodes representative of biological elements, and relationship descriptors describing relationships between nodes, the nodes and relationship descriptors in the database comprising a collection of biological assertions from which one or more candidate biological assertions are chosen. After selecting a target node in the database for investigation, a perturbation is specified for the target node. In response, given nodes and relationship descriptors of the database that potentially affect or are affected by the target node are traversed. In response to data generated during the traversing step, candidate biological assertions can be identified for further analysis. These biological assertions, and the nodes described therein, comprise the signature of interest for the target node (i.e., the signature's reference node).

Aspects of this disclosure may be practiced, typically in software, on one or more machines or computing devices.

Generalizing, a machine or computing device (a "computing entity") typically comprises commodity hardware and software, storage (e.g., disks, disk arrays, and the like) and memory (RAM, ROM, and the like). The particular computing entities used in the system are not a limitation of the disclosed subject matter. A given machine includes network interfaces and software to connect the machine to a network in the usual manner. The subject matter or features thereof may be implemented as a standalone product, or as a managed service using a set of machines, which are connected or connectable to one or more networks. More generally, the product or service is provided using a set of one or more computing-related entities (systems, machines, processes, programs, libraries, functions, or the like) that together facilitate or provide the inventive functionality described above. In a typical implementation, the service comprises a set of one or more computers. A representative machine is a network-based server running commodity (e.g. Pentium-class) hardware, an operating system (e.g., Linux, Windows, OS-X, or the like), an application runtime environment (e.g., Java, .ASP), and a set of applications or processes (e.g., AJAX technologies, Java applets or servlets, linkable libraries, native code, or the like, depending on platform), that provide the functionality of a given system or subsystem. A display may be used to provide an output. As described, the product or service (or any function thereof) may be implemented in a standalone server, or across a distributed set of machines, or in any a tablet or handheld computing device. Typically, a server or computing device connects to the publicly-routable Internet, an intranet, a private network, or any combination thereof, depending on the desired implementation environment.

According to another aspect, a computer program product comprising computer-readable instructions is provided. The computer-readable instructions, when loaded and executed on a computer system, cause the computer system to operate according to the various computational methods described above.

More generally, the techniques described herein are provided using a set of one or more computing-related entities (systems, machines, processes, programs, libraries, functions, or the like) that together facilitate or provide the described functionality described above. In a typical implementation, a representative machine on which the software executes comprises commodity hardware, an operating system, an application runtime environment, and a set of applications or processes and associated data, that provide the functionality of a given system or subsystem. As described, the functionality may be implemented in a stand-alone machine, or across a distributed set of machines.

A computing platform in which aspects of this disclosure may be practiced comprises co-located hardware and software resources, or resources that are physically, logically, virtually and/or geographically distinct. Communication networks used to communicate to and from the platform may be packet-based, non-packet based, and secure or non-secure, or some combination thereof.

One or more functions of such a technology platform may be implemented in a cloud-based architecture. As is well-known, cloud computing is a model of service delivery for enabling on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. Available services models that may be leveraged in whole or in part include: Software as a Service (SaaS) (the provider's applications running on cloud infrastructure); Platform as a service (PaaS) (the customer deploys applications that may be created using provider tools onto the cloud infrastructure); Infrastructure as a Service (IaaS) (customer provisions its own processing, storage, networks and other computing resources and can deploy and run operating systems and applications).

While given components of a computing entity or system have been described separately, one of ordinary skill will appreciate that some of the functions may be combined or shared in given instructions, program sequences, code portions, and the like.

The above-described mathematical derivations are intended to be representative and non-limiting. The techniques may be used, among other ways, to quantify assessment of biological impact of active substances, to characterize biological network response, to mechanistically assess the biological impact of a complex perturbation of an in vivo system, or the like. The approach herein facilitates a unified and coherent framework for scoring biological entities ranging from individual molecular mechanisms to systems-level processes, as well as methods for computing scores for each level. As has been described, a score represents an objective assessment of a degree of activation based on the known effects of that activity, e.g., differential expression of genes, differential levels or activities of other biological molecules (e.g., proteins), or the like. The quantitative methodology described herein provides comprehensive mechanistic insights into the biological response to exposures measured by transcriptomics. One possible utility of this methodology is to provide a comparative assessment of the biological impact of different therapeutic agents in order to understand their relative effects on a range of biological processes (including both therapeutically relevant and irrelevant processes). Further, the biological impact of environment exposures of consumer products could be assessed as a novel approach for systems toxicology.

Thus, for example, one application of the above-described network scoring methodology is for the evaluation of the possible effects of exposure to environmental toxins. In such a scenario, the biological networks represent various pathways for sensing and reacting to cell stresses, such as the oxidative stress response, DNA damage response, and apoptosis signaling pathways. Transcriptomic data is collected from an experiment where cell lines or animal models are exposed to a toxin of interest, and network scores are computed from this transcriptomic data. The specific network scores are then used to assess which biological pathways are affected by the toxin. Additionally, the network scores may be compared across different toxins to evaluate and/or rank the relative effects of the toxins on different pathways. For example, toxins could be ranked from highest to lowest scores for an oxidative stress pathway to determine which toxins are potentially stronger inducers of oxidative stress. Across a range of biological networks, such an approach provides an assessment of the relative impacts of various toxins on different pathways, providing a means of comparing the toxicity profiles of toxins and estimating exposure limits of one toxin by comparing its network and subnetwork scores to those of another toxin with known exposure effects and toxicity limits.

Another example application is in the evaluation of the effects of therapeutic drugs or treatments. Appropriate experimental systems (for example, cell lines or animal models) are treated with a drug, and transcriptomic data is collected. Networks representing the target pathway (or pathways) of a drug are scored to assess the impact of a drug, and networks representing related signaling pathways are scored to examine potential off-target effects of the drug. Furthermore, networks representing various stress and toxicity pathways may be scored to assess potential toxicity effects of the drug. Finally, various doses of a single drug, or various drugs targeting the same pathway (or pathways) are compared for their effects in the target pathway(s), related pathways, and toxicity pathways to identify doses or drugs with desired effects.

These are merely representative use cases.

Having described our invention, what we now claim is set forth below:

1. A method to determine a score for a degree of activation of an original network that is causally inconsistent, the original network composed of causal connections among a set of nodes that represent biological entities, biological processes or other biological networks, the original network having a reference node, comprising:
   (a) constructing, from the original network, a tree graph of tree-depth 1 comprising a root node and a set of child nodes, wherein the root node of the tree graph represents the original network, the tree graph represents the biological entities, the biological processes, and the other biological networks represented by the original network, the original network is causally inconsistent, and wherein each child node in the tree graph represents a particular node from the set of nodes in the original network and is connected to the root node by a signed, directed edge pointing from the root node to that child node;
   (b) determining, for each signed, directed edge connecting the root node to a respective child node in the tree graph representing a first respective particular node in the original network, a respective sign based on one of a net sign of a respective shortest path connecting the first respective particular node in the original network to the reference node in the original network, a set of signed spanning trees based on the original network, or a plurality of random walks along the original network;
   (c) determining, for each child node in the tree graph representing a second respective particular node in the original network, a respective weight based on one of a respective shortest path connecting the second respective particular node in the original network to the reference node in the original network, the set of signed spanning trees, or the plurality of random walks along the original network; and
   (d) scoring the tree graph based on a respective score and the respective weight assigned to each child node in the tree graph and the respective signs of each of the signed, directed edges;
   wherein the steps of the method are implemented in software executing in a hardware element.

2. The method of claim 1, wherein, the respective weight associated with at least one child node of the set of child nodes in the tree graph has a non-negative real value other than 1.

3. The method of claim 1, wherein the set of child nodes in the tree graph represent measurable biological entities or measurable biological processes, and the respective score assigned to each child node in the tree graph represents measurements of the measurable biological entities or the measurable biological processes.

4. The method of claim 1, wherein at least one child node in the tree graph represents another tree graph, wherein the another tree graph has a first score based on one or more measurable biological entities or measurable biological processes which comprise the another tree graph.

5. The method of claim 1, wherein the scoring is at least one of Network Perturbation Amplitude (NPA) or Geometric Perturbation Index (GPI).

6. The method of claim 1, wherein a length of the respective shortest path is determined by biasing edge lengths, wherein an edge length is biased by a value of an attribute.

7. The method of claim 2, further comprising:
enumerating tae set of signed spanning trees from the original network, wherein each spanning tree comprises a respective first set of nodes, and each node of the respective first set of nodes has a first respective sign based on a respective net sign of a respective path connecting a corresponding node to the reference node in the original network.

8. The method of claim 7, wherein the respective sign and the respective weight associated with each child node in the tree graph are based on a second respective sign associated with the respective particular node in the original network represented by the child node in the tree graph in a largest number of signed spanning trees of the set of signed spanning trees.

9. The method of claim 8, wherein the respective weight associated with each child node in the tree graph is computed as an absolute value of a given function $((N_+-N_-)/(N_++N_-))$, wherein $N_+$ is a first number of random walks to first nodes in the original network with positive signs and $N_-$ is a second number of random walks to second nodes in the original network with negative signs.

10. The method of claim 2, further comprising:
performing the plurality of random walks along the original network, each random walk initiated at the reference node, and
for each random walk, determining a first respective sign and a first respective weight associated with a respective child node in the tree graph representing a respective particular node based on a second respective sign associated with the particular node in the original network.

11. The method of claim 10, wherein each random walk is biased based on attributes of edges in the original network.

12. A non-transitory computer program product comprising computer-readable instructions that, when loaded and executed on a computer system, cause the computer system to operate to determine a score for a degree of activation of an original network that is causally inconsistent, the original network composed of causal connections among a set of nodes that represent biological entities, biological processes, or other biological networks, the original network having a reference node, the computer-readable instructions comprising program code configured to:
construct a tree graph of tree-depth 1 comprising a root node and a set of child nodes, wherein the root node of the tree graph represents the original network, the tree graph represents the biological entities, the biological processes, and the other biological networks represented by the set of nodes, and the original network is causally inconsistent, and wherein each child node in the tree graph represents a particular node from the set of nodes in the original network and is connected to the root node by a signed, directed edge pointing from the root node to that child node in the tree graph;
determine, for each signed, directed edge connecting the root node to a respective child node in the tree graph representing a first respective particular node from the set of nodes in the original network, a respective sign based on one of a net sign of a respective shortest path connecting the first respective particular node in the original network to the reference node in the original network, a set of signed spanning trees based on the original network, or a plurality of random walks along the original network;
determine, for each child node in the tree graph representing a second respective particular node from the set of nodes in the original network, a respective weight based on one of the shortest path connecting the particular node in the original network to the reference node in the original network, the set of signed spanning trees, or the plurality of random walks; and
score the tree graph based on a respective score and the respective weight assigned to each child node in the tree graph and the respective sign of each of the signed, directed edges.

13. The non-transitory computer program product of claim 12, wherein the respective weight associated with at least one child node of the set of child nodes in the tree graph has a non-negative real value other than 1.

14. The non-transitory computer program product of claim 12, wherein the set of child nodes in the tree graph represent measurable biological entities or measurable biological processes, and the respective score assigned to each child node in the tree graph represents measurements of the measurable biological entities or the measurable biological processes.

15. The non-transitory computer program product of claim 12, wherein at least one child node in the tree graph represents another tree graph, the another tree graph having a first score on one or more measurable biological entities or measurable biological processes which comprise the another tree graph.

16. The non-transitory computer program product of claim 12, wherein the scoring is at least one of Network Perturbation Amplitude (NPA) or Geometric Perturbation Index (GPI).

17. The non-transitory computer program product of claim 12, wherein a sign relationship between a given pair of nodes in the tree graph is determined by averaging over a sample of spanning trees constructed using random walks over the tree graph.

18. A method for applying network perturbation amplitude ("NPA") scoring to a causally inconsistent network composed of a set of edges connecting a set of nodes representing biological entities, biological processes, or biological networks the method comprising:
constructing, by at least one processor, a tree graph of tree-depth one from the causally inconsistent network, the tree graph representing the biological entities, the biological processes, and the other biological networks represented by the causally inconsistent network, the tree graph comprising a root node and a set of child nodes, each child node in the set of child nodes in the tree graph connected to the root node by a respective directed edge, wherein the set of nodes in the causally inconsistent network are divided into a reference node and a set of particular nodes, each child node in the set of child nodes in the tree graph corresponding to a respective particular node in the set of particular nodes from the causally inconsistent network;
enumerating, by the at least one processor, a set of signed spanning trees by performing a plurality of random walks starting from the reference node in the causally inconsistent network, wherein each random walk from the plurality of random walks produces a respective signed spanning tree of the set of signed spanning trees;

determining, by the at least one processor and for each directed edge, a respective sign, and, for each child node in the tree graph, a respective weight, based on the set of signed spanning trees;

determining, by the at least one processor, a score for the causally inconsistent network by performing NPA scoring on the tree graph to determine a tree graph score based on a respective node score and the respective weight of each child node and the respective sign of each directed edge, the score being the tree graph score.

19. The method of claim 18, wherein the respective weight associated with each child node in the tree graph is computed as an absolute value of a given function (($N_+ - N_-$)/($N_+ + N_-$)), wherein $N_+$ is a first number of random walks from the plurality of random walks to first nodes in the causally inconsistent network with positive signs and $N_-$ is a second number of random walks from the plurality of random walks to second nodes in the causally inconsistent network with negative signs.

20. The method of claim 18, wherein the respective sign of each directed edge connected to a respective child node in the tree graph is based on a matching respective sign associated with the respective particular node in the original network represented by the respective child node in the tree graph in a largest number of signed spanning trees of the set of signed spanning trees.

* * * * *